United States Patent [19]

Boeckx et al.

[11] Patent Number: 4,778,887
[45] Date of Patent: Oct. 18, 1988

[54] α-ARYL-4-(4,5-DIHYDRO-3,5-DIOXO-1,2,4-TRIAZIN-2(3H)-YL)-BENZENEACETONITRILES

[75] Inventors: Gustaaf M. Boeckx, Oud-Turnhout; Alfons H. M. Raeymaekers, Beerse; Victor Sipido, Merksem, all of Belgium

[73] Assignee: Janssen Pharmaceutica N.V., Beerse, Belgium

[21] Appl. No.: 920,016

[22] Filed: Oct. 17, 1986

Related U.S. Application Data

[60] Division of Ser. No. 748,075, Jun. 24, 1985, Pat. No. 4,631,278, which is a continuation-in-part of Ser. No. 636,538, Aug. 1, 1984, abandoned.

[51] Int. Cl.$^4$ ............................................. C07D 253/06
[52] U.S. Cl. ................................... 544/182; 544/221; 558/394; 558/404; 558/406
[58] Field of Search ............... 544/182, 221; 558/394, 558/404, 406

Primary Examiner—Mary C. Lee
Assistant Examiner—J. G. Mullins
Attorney, Agent, or Firm—Geoffrey G. Dellenbaugh

[57] ABSTRACT

The present invention is related with α-aryl-4-(4,5-dihydro-3,5-dioxo-1,2,4-triazin-2(3H)-yl)benzeneacetonitriles which are effective in destructing or preventing the growth of Protozoa in subjects suffering from such Protozoa.

7 Claims, No Drawings

α-ARYL-4-(4,5-DIHYDRO-3,5-DIOXO-1,2,4-TRIAZIN-2(3H)-YL)-BENZENEACETONITRILES

CROSS-REFERENCE TO RELATED APPLICATIONS

This is a divisional of our co-pending application Ser. No. 748,075, filed June 24, 1985, now U.S. Pat. No. 4,631,278, which in turn is a continuation-in-part of our application Ser. No. 636,538, filed Aug. 1, 1984, now abandoned.

BACKGROUND OF THE INVENTION

2-Phenyl-as-triazine-3,5-(2H,4H)diones and their use for controlling coccidiosis have been described in U.S. Pat. No. 3,912,723. The phenyl moiety in the said triazines may, inter alia, be substituted with a benzoyl-, a α-hydroxy-phenylmethyl- and a phenylsulfonyl radical. The 2-phenyl-as-triazine-3,5-(2H,4H)diones, described in the present application, differ from the hereinabove-mentioned triazinones, by the substitution of the phenyl moiety with a α-cyano-phenylmethyl radical, resulting in triazine-3,5-(2H,4H)-diones which are very effective in destructing or preventing the growth of Protozoa in subjects suffering from such Protozoa.

DESCRIPTION OF THE PREFERRED EMBODIMENTS

The present invention is related with α-aryl-4-(4,5-dihydro-3,5-dioxo-1,2,4-triazin-2(3H)-yl)benzeneacetonitriles having the formula

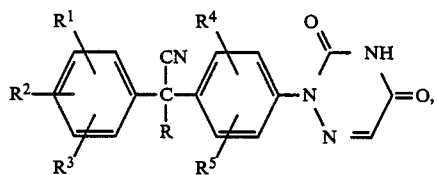

the pharmaceutically acceptable acid addition salts and the possible stereochemically isomeric forms thereof, wherein:

$R^1$, $R^2$ and $R^3$ are each independently hydrogen, halo, trifluoromethyl, $C_{1-6}$ alkyl, $C_{1-6}$ alkyloxy, $C_{1-6}$ alkylthio or $C_{1-6}$ alkylsulfonyl;

$R^4$ and $R^5$ are each independently hydrogen, halo, trifluoromethyl or $C_{1-6}$ alkyl; and R is hydrogen, $C_{1-6}$ alkyl, cyclo $C_{3-6}$ alkyl or phenyl optionally substituted with up to three substituents each independently selected from the group consisting of halo, trifluoromethyl, $C_{1-6}$ alkyl, $C_{1-6}$ alkyloxy, $C_{1-6}$ alkylthio and $C_{1-6}$ alkylsulfonyloxy.

In the foregoing definitions the term "halo" is generic to fluoro, chloro, bromo and iodo; "$C_{1-6}$ alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; "cyclo $C_{3-6}$ alkyl" embraces cyclopropyl, cyclobutyl, cyclopentyl and cyclohexyl.

Preferred compounds within the invention are those wherein $R^1$ and $R^2$ are, each independently, hydrogen, halo, $CF_3$, or $C_{1-6}$ alkyl; $R^3$ is hydrogen, $C_{1-6}$ alkyl, phenyl or halophenyl; $R^4$ and $R^5$ are, each independently, hydrogen, halo, $CF_3$ or $C_{1-6}$ alkyl.

More preferred compounds within the invention are those wherein $R^1$ is halo; $R^2$ and $R^3$ are both hydrogen; R is hydrogen, $C_{1-6}$ alkyl or halophenyl; and $R^4$ and $R^5$ are as described hereinabove for the preferred compounds.

Particularly preferred compounds within the invention are those wherein $R^1$ is 4-halo, $R^2$ and $R^3$ are both hydrogen, R is hydrogen or methyl and $R^4$ and $R^5$ are each independently hydrogen, halo, methyl or trifluoromethyl, said $R^4$ and $R^5$ are being substituted on the 2 and/or 6 position of the phenyl moiety bearing said $R^4$ and $R^5$.

The most preferred compounds of the present invention are selected from the group consisting of 2-chloro-α-(4-chlorophenyl)-4-(4,5-dihydro-3,5-dioxo-1,2,4-triazin-2(3H)-yl)benzeneacetonitrile and 2,6-dichloro-α-(4-chlorophenyl)-4-(4,5-dihydro-3,5-dioxo-1,2,4-triazin-2(3H)-yl)benzeneacetonitrile, the pharmaceutically acceptable acid-addition salts and possible stereochemically isomeric forms thereof.

The compounds of formula (I) may generally be prepared by cyclizing an intermediate of formula

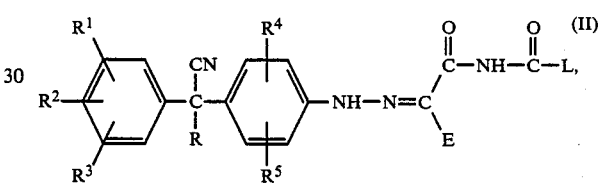

and eliminating the group E of the thus obtained dione

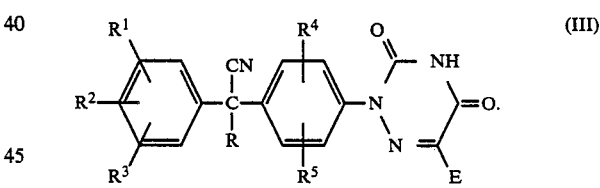

In the intermediates (II) L has the meaning of an appropriate leaving group such as $C_{1-6}$ alkyloxy, halo and the like. The group E, as described in the intermediate (II) and the triazinedione (III), represents an appropriate electron attracting group which may conveniently be eliminated from the dione (III) such as, for example, a carboxyl, a sulfonyloxy, a sulfinyloxy group or a precursor and/or derivative thereof, e.g. an ester, an amide, a cyanide, a $C_{1-6}$ alkylsulfonyloxy, phenylsulfonyloxy, $C_{1-6}$ alkylphenylsulfonyloxy and halophenylsulfonyloxy and the like like groups.

A particularly suitable process for preparing compounds of formula (I) consists of cyclizing an intermediatee of formula (II-a) and eliminating the $E^1$ functionality in the thus obtained intermediate of formula (III-a). In (II-a) and (III-a) $E^1$ represents a cyano, $C_{1-6}$ alkyloxycarbonyl or amido group.

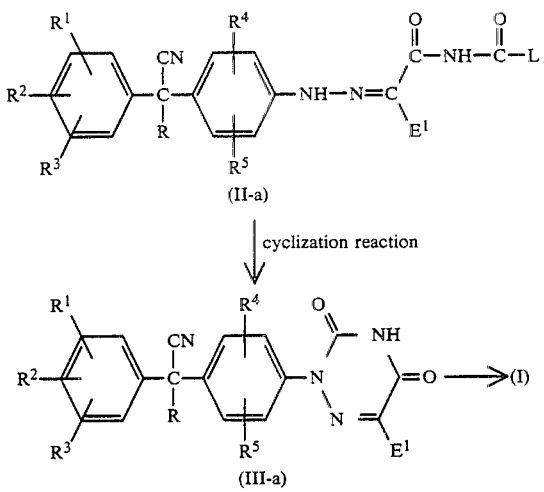

The cyclization reaction may be effected following art-known cyclization procedures as described, for example, in Monatshefte der Chemie, 94, 258–262 (1963), e.g. by heating the starting compound of formula (II-a) over its melting point, or by refluxing a mixture of (II-a) with a suitable solvent such as, for example, an aromatic hydrocarbon, e.g. benzene, methylbenzene, or dimethylbenzene, an acid, e.g. acetic acid, optionally in the presence of base, e.g. potassium acetate, sodium acetate and the like.

The elimination of the $E^1$ functionality may be effected following art-known procedures as described, for example, in Monatshefte der Chemie, 96, 134–137 (1965), e.g. by converting (III-a) into a carboxylic acid (IV) in a suitable acidic reaction medium such as acetic acid, aqueous hydrochloric acid solutions or mixtures thereof. Elevated temperatures may enhance the rate of the reaction. The thus obtained carboxylic acids of formula

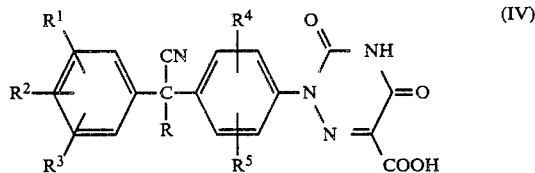

may be converted into a compound of formula (I) by art-known decarboxylation reaction procedurs, e.g. by heating the carboxylic acid (IV) or by heating a solution of (IV) in 2-mercaptoacetic acid as described, for example, in U.S. Pat. No. 3,896,124.

The compounds of formula (I) may also generally be prepared by converting the hydroxyl function of a triazinedione of formula

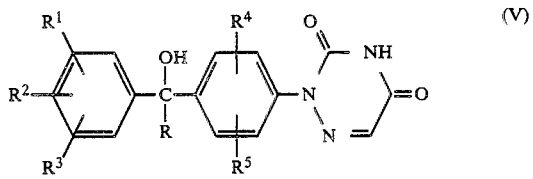

into a nitrile function.

The conversion of (V) into (I) may be effected by art-known procedures. For example, by first converting the hydroxy function into a suitable leaving group and subsequently converting the said leaving group in the thus obtained

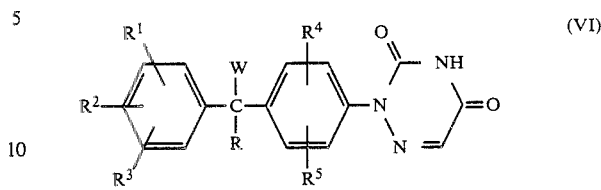

into a nitrile function.

In (VI) W has the meaning of an appropriate reactive leaving group such as, for example, halo, e.g., chloro, bromo or iodo, or a sulfonyloxy group, e.g. methylsulfonyloxy or 4-methylphenylsulfonyloxy.

For example, where W represents chloro, the intermediates (VI) may be prepared by reacting (V) with thionyl chloride in a suitable reaction-inert solvent.

The conversion of (VI) into (I) may be effected, for example, by reacting (VI) with a cyanide, such as, for example, a alkalimetal cyanide, e.g. potassium cyanide, sodium cyanide; copper cyanide; silver cyanide and the like, if desired, in the presence of an appropriate solvent.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

It is obvious from formula (I) that the compounds of the present invention have an asymmetric carbon atom. Consequently, these compounds may exist under two different enantiomeric forms. Pure enantiomeric forms of the compounds of formula (I) may be obtained by the application of art-known procedures.

A number of intermediates and starting materials in the foregoing preparations are known compounds which may be prepared according to art-known methodologies of preparing said or similar compounds. A number of such preparation methods will be described hereinafter in more detail.

The intermediates of formula (III) may generally be prepared by reacting a diazonium salt of formula (VII) with a reagent of formula (VIII).

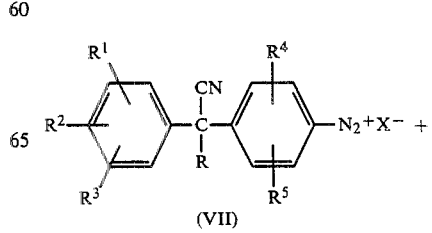

-continued

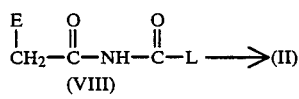

$X^-$, as described in (VII) has the meaning of an appropriate anion and E and L, as described in (VIII), have the previously defined meanings.

The reaction of (VII) with (VIII) may conveniently be conducted in a suitable reaction medium as described, for example, in Monatschefte der Chemie, 94, 694–697 (1963). Suitable reaction mediums are, for example, aqueous sodium acetate solutions, pyridine and the like.

The starting diazonium salts (VII) may be derived from a corresponding amine of formula (IX) following art-known procedures by reacting the latter with an alkalimetal or earth alkaline metal nitrite, e.g. sodium nitrite, in a suitable reaction medium.

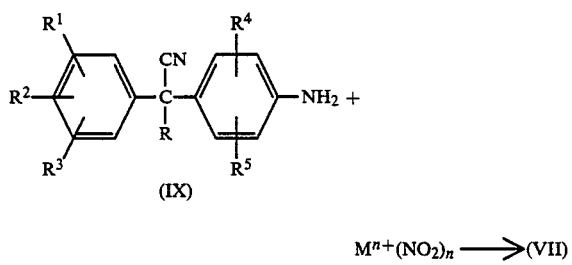

In the hereinabove-described reaction scheme $M^{n+}$ is a alkalimetal or earth alkaline metal kation and n is the integer 1 or 2.

The amines of formula (IX) may be prepared following procedures analogous to those described in U.S. Pat. No. 4,005,218.

The triazinediones of formula (VI) may be prepared following the procedures described in U.S. Pat. No. 3,912,723.

The intermediates of formula (II) and (III), and more particularly, the intermediates of formula (II-a), (III-a) and (IV), said intermediates being useful in the preparation of the compounds of formula (I), are deemed to be novel and this constitutes an additional feature of the present invention.

The compounds of formula (I), the pharmaceutically acceptable acid addition salts and the possible stereochemically isomeric forms thereof are useful agents in combatting Protozoa. For example, said compounds are found to be active against a wide variety of said Protozoa such as, for example, Sarcodina, Mastigophora, Ciliophora and Sporozoa.

The compounds of formula (I), the pharmaceutically acceptable acid addition salts and the possible stereochemically isomeric forms thereof are especially useful agents in combatting Rhizopoda such as, for example, Entamoeba; and Mastigophora such as, for example, Trichomonas, e.g. *Trichomonas vaginalis*, Histomonas, e.g. *Histomonas maleagridis*, and Trypanosoma spp.

In view of their potent activity in combatting Protozoa the compounds of this invention constitute useful tools for the destruction or prevention of the growth of Protozoa and more particularly they can effectively be used in the treatment of subjects suffering from such Protozoa.

In view of the potent activity in combatting Protozoa this invention provides valuable compositions comprising the compounds of formula (I), the acid addition salts or possible stereochemically isomeric forms thereof, as the active ingredient in a solvent or a solid, semi-solid or liquid diluent or carrier, and, in addition, it provides an effective method of combatting Protozoa by use of an effective anti-protozoal amount of such compounds of formula (I), or acid addition salts thereof. Antiprotozoal compositions comprising an effective amount of an active compound of formula (I), either alone or in combination with other active therapeutic ingredients, in admixture with suitable carriers may be readily prepared according to conventional pharmaceutical techniques for the usual routes of administration.

Preferred compositions are in dosage unit form, comprising per dosage unit an effective quantity of the active ingredient in admixture with suitable carriers. Although the amount of the active ingredient per unit dosage may vary within rather wide limits, dosage units comprising from about 10 to about 2000 mg of the active ingredient are preferred.

In view of the anti-protozoal properties of the compounds of formula (I) it is evident that the present invention provides a method of inhibiting and/or eliminating the development of Protozoa in warm-blooded animals suffering from diseases caused by one or more of those Protozoa by the administration of an antiprotozoal effective amount of a compound of formula (I), a pharmaceutically acceptable acid addition salt or a possible stereochemically isomeric form thereof.

More particularly, in view of their extremely potent activity in combatting Coccidia the compounds of this invention are very useful in the destruction or prevention of the growth of Coccidia in warm-blooded animals. Consequently, the compounds of formula (I), the acid addition salts and possible stereochemically isomeric forms thereof are particularly useful anti-coccidial agents as well as coccidiostatics.

Due to their useful anti-coccidial and coccidiostatic activity the subject compounds may be administered in combination with any solid, semi-solid or liquid diluent or carrier as described hereinabove. Additionally, due to their useful coccidiostatic activity the subject compounds may be mixed with any kind of feed supplied to warm-blooded animals although it may also be administered while dissolved or suspended in the drinking water.

The following examples are intended to illustratee and not to limit the scope of the present invention. Unless otherwise stated all parts therein are by weight.

EXAMPLES (A) Preparation of Intermediates

EXAMPLE 1

A mixture of 68 parts of 4-fluorobenzeneacetonitrile, 180 parts of ethyl carbonate, 100 parts of a sodium methoxide solution 30% and 200 parts of dimethylbenzene was distilled till an internal temperature of 110° C. was reached. The distillate was cooled and 80 parts of 2-propanol were added, followed by the dropwise addition of 63 parts of methyl sulfate at room temperature (exothermic reaction: temperature rose to 80° C.). The remaining 120 parts of 2-propanol were added while stirring vigorously. Upon completion, stirring was continued for 20 hours. Then there were added 56 parts of potassium hydroxide (exothermic reaction: temperature rose to 75° C.). The whole was stirred and refluxed for 30 minutes. The reaction mixture was cooled and poured into 750 parts of water. The aqueous phase was separated and extracted with methylbenzene. The extract was dried, filtered and evaporated. The oily residue was distilled, yielding 54 parts of 4-fluoro-α-methylbenzeneacetonitrile; bp. 110°–115° C. at 11 mm. pressure (intermediate 1).

EXAMPLE 2

To a stirred solution of 20 parts of 1,2-dichloro-4-nitrobenzene in 160 parts of pyridine was added a paste of 28 parts of solid potassium hydroxide and 40 parts of pyridine. After cooling to 5° C., there was added dropwise 15.6 parts of 4-fluoro-α-methylbenzeneacetonitrile. Upon completion, the whole was further stirred for 10 hours at −5° C. The cooling bath was removed and the reaction mixture was diluted with 80 parts of benzene. The whole was filtered and the filtrate was evaporated. The residue was poured into water and the product was extracted with methylbenzene. The latter was dried, filtered and evaporated. The solid residue was crystallized from a mixture of 1,1′-oxybisethane and benzene, yielding 15 parts of α-(2-chloro-4-nitrophenyl)-4-fluoro-α-methylbenzeneacetonitrile; mp. 133.1° C. (intermediate 2).

EXAMPLE 3

To a stirred mixture of 45.3 parts of 1,2,3-trichloro-5-nitrobenzene, 300 parts of a sodium hydroxide solution 50%, 5 parts of N,N,N-triethylbenzenemethanaminium chloride and 360 parts of tetrahydrofuran was added dropwise, during a 5 minute period, a solution of 33.3 parts of 4-chlorobenzeneacetonitrile in 90 parts of tetrahydrofuran. Upon completion, stirring was continued for 4 hours at 50° C. The reaction mixture was poured into 1500 parts of crushed ice and acidified with concentrate hydrochloric acid. The product was extracted with trichloromethane. The extract was dried, filtered and evaporated. The residue was stirred in 2,2′-oxybispropane. The product was filtered off and dried, yielding 63.8 parts (93.3%) of 2,6-dichloro-α-(4-chlorophenyl)-4-nitrobenzeneacetonitrile (intermediate 3).

Following the same procedure and using equivalent amounts of the appropriate starting materials, there were also prepared:

4-chloro-α-(2-chloro-4-nitrophenyl)-α-methylbenzeneacetonitrile; mp. 139.3° C. (intermediate 4);
2-chloro-α-(4-chlorophenyl)-4-nitrobenzeneacetonitrile (intermediate 5);
α-(4-chlorophenyl)-α-methyl-4-nitro-2-(trifluoromethyl)benzeneacetonitrile (intermediate 6);
2-chloro-α,α-bis(4-chlorophenyl)-4-nitrobenzeneacetonitrile (intermediate 7);
2-chloro-α-(4-chlorophenyl)-5-methyl-4-nitrobenzeneacetonitrile (intermediate 8);
2-fluoro-α-(4-fluorophenyl)-4-nitrobenzeneacetonitrile (intermediate 9);
2,6-dichloro-α-(4-fluorophenyl)-4-nitrobenzeneacetonitrile (intermediate 10);
2-chloro-α-(4-fluorophenyl)-6-methyl-4-nitrobenzeneacetonitrile (intermediate 11);
α-(4-fluorophenyl)-2,6-dimethyl-4-nitrobenzeneacetonitrile (intermediate 12); and
2-chloro-α-(4-chlorophenyl)-5-methyl-4-nitrobenzeneacetonitrile (intermediate 13).

Following the same procedures and using the appropriate starting materials there are also prepared:

2-chloro-α-(4-chlorophenyl)-6-methyl-4-nitrobenzeneacetonitrile (intermediate 14);
2-chloro-α-(4-fluorophenyl)-4-nitrobenzeneacetonitrile (intermediate 15); and
2-chloro-α-(4-methylphenyl)-4-nitrobenzeneacetonitrile (intermediate 16).

EXAMPLE 4

To a stirred mixture of 14.2 parts of iodomethane, 153 parts of a sodium hydroxide solution 50%, 1 part of N,N,N-triethylbenzenemethanaminium chloride and 67.5 parts of tetrahydrofuran was added dropwise, during a period of 15 minutes, a solution of 37.5 parts of 2-chloro-α-[4-chloro-3-(trifluoromethyl)phenyl]-4-nitrobenzeneacetonitrile in 67.5 parts of tetrahydrofuran. The reaction mixture was stirred and heated for 4 hours at 50°–60° C. Another portion of 2.3 parts of iodomethane was added and the whole was stirred for 1 hour at 50° C. The mixture was poured into 1000 parts of crushed ice. The whole was acidified with concentrate hydrochloric acid. The product was extracted with trichloro-methane. The extract was dried, filtered and evaporated. The residue was stirred in 160 parts of ethanol. The product was filtered off, washed with 2,2′-oxybispropane and dried, yielding 34.2 parts (87.8%) of 4-chloro-α-(2-chloro-4-nitrophenyl)-α-methyl-3-(trifluoromethyl)benzeneacetonitrile; mp. 162.5° C. (intermediate 17).

In a similar manner there were also prepared:
2-chloro-α-(4-chlorophenyl)-4-nitro-α-propylbenzeneacetonitrile (intermediate 18);
α-butyl-2-chloro-α-(4-chlorophenyl)-4-nitrobenzeneacetonitrile (intermediate 19);
2,6-dichloro-α-(4-chlorophenyl)-α-methyl-4-nitrobenzeneacetonitrile (intermediate 20);
2-chloro-α-(4-chlorophenyl)-α,6-dimethyl-4-nitrobenzeneacetonitrile (intermediate 21);
2-chloro-α-(4-chlorophenyl)-α,5-dimethyl-4-nitrobenzeneacetonitrile (intermediate 22); and
2-fluoro-α-(4-fluorophenyl)-α-methyl-4-nitrobenzeneacetonitrile (intermediate 23).

EXAMPLE 5

A mixture of 20 parts of 4-chloro-α-(2-chloro-4-nitrophenyl)-α-methylbenzeneacetonitrile, 7 parts of iron powder, 250 parts of ammonium chloride solution 0.78N and 200 parts of methylbenzene was stirred and refluxed for 3 hours. The reaction mixture was filtered hot. The aqueous phase was separated and washed with methylbenzene. The combined organic layers were washed successively with water, sodium hydrogen carbonate solution and again with water, dried and evaporated. The residue was washed with 1,1′-oxybisethane and dried, yielding 10 parts of α-(4-amino-2-chlorophenyl)-4-chloro-α-methylbenzeneacetonitrile; mp. 135.2° C. (intermediate 24).

In a similar manner there was also prepared:
α-(4-amino-2-chlorophenyl)-4-fluoro-α-methylbenzeneacetonitrile; mp. 121.2° C. (intermediate 25).

EXAMPLE 6

A mixture of 31.1 parts of 4-chloro-α-(2-chloro-4-nitrophenyl)-α-methyl-3-(trifluoromethyl)benzeneacetonitrile, 2 parts of a solution of thiophene in methanol 4% and 480 parts of methanol was hydrogenated in the Parr apparatus at 50° C. with 3 parts of platinum-on-charcoal catalyst 5%. After the calculated amount of hydrogen was taken up, the catalyst was filtered off, washed with tetrahydrofuran and the filtrate was evaporated in vacuo. The residue was crystallized from 160 parts of 2-propanol. The product was filtered off, washed with 2,2'-oxybispropane and dried, yielding 23.7 parts (82.4%) of (4-amino-2-chloro-α-[4-chloro-3-(trifluoromethyl)phenyl]-α-methylbenzeneacetonitrile; mp. 180.4° C. (intermediate 26).

In a similar manner there was also prepared:
4-amino-α-(4-chlorophenyl)-α-methyl-2-(trifluoromethyl)benzeneacetonitrile (intermediate 27);
4-amino-2-chloro-α,α-bis(4-chlorophenyl)benzeneacetonitrile (intermediate 28);
4-amino-2-chloro-α-(4-chlorophenyl)-α-propylbenzeneacetonitrile (intermediate 29);
4-amino-α-butyl-2-chloro-α-(4-chlorophenyl)benzeneacetonitrile (intermediate 30);
4-amino-2,6-dichloro-α-(4-chlorophenyl)-α-methylbenzeneacetonitrile (intermediate 31);
4-amino-2-chloro-α-(4-chlorophenyl)-α,6-dimethylbenzeneacetonitrile (intermediate 32);
4-amino-2-chloro-α-(4-chlorophenyl)-α,5-dimethylbenzeneacetonitrile (intermediate 33);
4-amino-2-fluoro-α-(4-fluorophenyl)-α-methylbenzeneacetonitrile (intermediate 34);
4-amino-2,6-dichloro-α-(4-fluorophenyl)benzeneacetonitrile (intermediate 35);
4-amino-2-chloro-α-(4-fluorophenyl)-6-methylbenzeneacetonitrile (intermediate 36);
4-amino-α-(4-fluorophenyl)-2,6-dimethylbenzeneacetonitrile (intermediate 37);
4-amino-α-(4-chlorophenyl)-2,6-dimethylbenzeneacetonitrile (intermediate 38);

Following the same procedures and using the appropriate starting materials there are also prepared:
4-amino-2-chloro-α-(4-chlorophenyl)benzeneacetonitrile (intermediate 39);
4-amino-2,6-dichloro-α-(4-chlorophenyl)benzeneacetonitrile (intermediate 40);
4-amino-2-chloro-α-(4-chlorophenyl)-6-methylbenzeneacetonitrile (intermediate 41);
4-amino-2-chloro-α-(4-fluorophenyl)benzeneacetonitrile (intermediate 42); and
4-amino-2-chloro-α-(4-methylphenyl)benzeneacetonitrile (intermediate 43).

EXAMPLE 7

To a stirred and cooled (5°–10° C.) mixture of 15.2 parts of 4-amino-2-chloro-α-(4-chlorophenyl)-α,5-dimethylbenzeneacetonitrile, 14.4 parts of concentrate hydrochloric acid and 125 parts of acetic acid was added dropwise, during a 30 minutes period, a solution of 3.5 parts of sodium nitrite in 15 parts of water at about 10° C. Upon completion, the whole was stirred for 30 minutes and then 10 parts of sodium acetate and 7.8 parts of ethyl (2-cyanoacetyl)carbamate were added, during a period of 2 hours, at room temperature. The reaction mixture was poured into 500 parts of water. The product was filtered off, washed with water and dissolved in dichloromethane. The organic layer was dried, filtered and evaporated. The residue was purified by column chromatography over silica gel using a mixture of trichloromethane and methanol (95:5 by volume) as eluent. The pure fractions were collected and the eluent was evaporated in vacuo. The residue was stirred in 2-propanol. The product was filtered off, washed with 2,2'-oxybispropane and dried, yielding 17.5 parts (74.1%) of ethyl[2-[[5-chloro-4-[1-(4-chlorophenyl)-1-cyanoethyl]-2-methylphenyl]hydrazono]-2-cyanoacetyl]carbamate (intermediate 44).

Following the same procedure and using equivalent amounts of the appropriate starting materials, there were also prepared:
ethyl[2-cyano-2-[[4-(1-cyano-1-phenylethyl)phenyl]hydrazono]acetyl]carbamate (intermediate 45);
ethyl[2-[[3-chloro-4-[1-(4-chlorophenyl)-1-cyanoethyl]phenyl]hydrazono]-2-cyanoacetyl]carbamate (intermediate 46);
ethyl[2-[2-[3-chloro-4-[1-cyano-1-(4-fluorophenyl)ethyl]phenyl]hydrazono]-2-cyanoacetyl]carbamate (intermediate 47);
ethyl[2-[[4-[1-(4-chlorophenyl)-1-cyanoethyl]-3-(trifluoromethyl)phenyl]hydrazono]-2-cyanoacetyl]carbamate (intermediate 48);
ethyl[2-[[4-[bis(4-chlorophenyl)cyanomethyl]-3-chlorophenyl]hydrazono]-2-cyanoacetyl]carbamate (intermediate 49);
ethyl[2-[[3-chloro-4-[1-(4-chlorophenyl)-1-cyanobutyl]phenyl]hydrazono]-2-cyanoacetyl]carbamate (intermediate 50);
ethyl[2-[[3-chloro-4-[1-(4-chlorophenyl)-1-cyanopentyl]phenyl]hydrazono]-2-cyanoacetyl]carbamate (intermediate 51);
ethyl[2-[[3-chloro-4-[1-[4-chloro-3-(tifluoromethyl)phenyl]-1-cyanoethyl]phenyl]hydrazono]-2-cyanoacetyl]carbamate (intermediate 52);
ethyl[2-[2-[4-[1-(4-chlorophenyl)-1-cyanoethyl]-3,5-dichlorophenyl]hydrazono]-2-cyanoacetyl]carbamate (intermediate 53);
ethyl[2-[[3-chloro-4-[1-(4-chlorophenyl)-1-cyanoethyl]-5-methylphenyl]hydrazono]-2-cyanoacetyl]carbamate (intermediate 54)
ethyl[2-cyano-2-[[4-[1-cyano-1-(4-fluorophenyl)ethyl]-3-fluorophenyl]hydrazono]acetyl]carbamate (intermediate 55);
ethyl[2-[[3,5-dichloro-4-[cyano(4-fluorophenyl)methyl]phenyl]hydrazono]-2-cyanoacetyl]carbamate (intermediate 56);
ethyl[2-[[3-chloro-4-[cyano(4-fluorophenyl)methyl]-5-methylphenyl]hydrazono]-2-cyanoacetyl]carbamate; (intermediate 57)
ethyl[2-cyano-2-[[4-[cyano(4-fluorophenyl)methyl]-3,5-dimethylphenyl]hydrazono]acetyl]carbamate (intermediate 58);
ethyl[2-[[4-[(4-chlorophenyl)cyanomethyl]-3,5-dimethylphenyl]hydrazono]-2-cyanoacetyl]carbamate (intermediate 59).

Following the same procedure and using the appropriate starting materials there are also prepared:
ethyl[2-[[3-chloro-4-[(4-chlorophenyl)cyanomethyl]phenyl]hydrazono]-2-cyanoacetyl]carbamate (intermediate 60);
ethyl[2-[[3,5-dichloro-4-[(4-chlorophenyl)cyanomethyl]phenyl]hydrazono]-2-cyanoacetyl]carbamate (intermediate 61);
ethyl[2-[[3-chloro-4-[(4-chlorophenyl)cyanomethyl]-5-methylphenyl]hydrazono]-2-cyanoacetyl]carbamate (intermediate 62);
ethyl[2-[[3-chloro-4-[(4-fluorophenyl)cyanomethyl]phenyl]hydrazono]-2-cyanoacetyl]carbamate (intermediate 63); and
ethyl[2-[[3-chloro-4-[(4-methylphenyl)cyanomethyl]phenyl]hydrazono]-2-cyanoacetyl]carbamate (intermediate 64).

EXAMPLE 8

A mixture of 7.8 parts of ethyl[2-cyano-2-[[4-(1-cyano-1-phenylethyl)phenyl]hydrazono]acetyl]carbamate, 1.98 parts of anhydrous potassium acetate and 120 parts of acetic acid was stirred and refluxed for 3 hours. The reaction mixture was concentrated to a volume of 30 parts. Water was added till the product was precipitated. It was sucked off, washed with water and dissolved in trichloromethane. The remaining water was separated and the organic phase was dried, filtered and evaporated, yielding 6.86 parts of 2-[4-(1-cyano-1-phenylethyl)phenyl]-2,3,4,5-tetrahydro-3,5-dioxo-1,2,4-triazine-6-carbonitrile as a residue (intermediate 65).

In a similar manner there was also prepared:

2-[3-chloro-4-[1-(4-chlorophenyl)-1-cyanoethyl]-phenyl]-2,3,4,5-tetrahydro-3,5-dioxo-1,2,4-triazine-6-carbonitrile (intermediate 66);

2-[3-chloro-4-[1-cyano-1-(4-fluorophenyl)ethyl]-phenyl]-2,3,4,5-tetrahydro-3,5-dioxo-1,2,4-triazine-6-carbonitrile (intermediate 67);

2-[4-[1-(4-chlorophenyl)-1-cyanoethyl]-3-(trifluoromethyl)phenyl]-2,3,4,5-tetrahydro-3,5-dioxo-1,2,4-triazine-6-carbonitrile (intermediate 68);

2-[4-[bis(4-chlorophenyl)cyanomethyl]-3-chloro-phenyl]-2,3,4,5-tetrahydro-3,5-dioxo-1,2,4-triazine-6-carbonitrile (intermediate 69);

2-[3-chloro-4-[1-(4-chlorophenyl)-1-cyanobutyl]-phenyl]-2,3,4,5-tetrahydro-3,5-dioxo-1,2,4-triazine-6-carbonitrile (intermediate 70);

2-[3-chloro-4-[1-(4-chlorophenyl)-1-cyanopentyl]-phenyl]-2,3,4,5-tetrahydro-3,5-dioxo-1,2,4-triazine-6-carbonitrile (intermediate 71);

2-[3-chloro-4-[1-[4-chloro-3-(trifluoromethyl)phenyl]-1-cyanoethyl]phenyl]-2,3,4,5-tetrahydro-3,5-dioxo-1,2,4-triazine-6-carbonitrile (intermediate 72);

2-[4-[1-(4-chlorophenyl)-1-cyanoethyl]-3,5-dichloro-phenyl]-2,3,4,5-tetrahydro-3,5-dioxo-1,2,4-triazine-6-carbonitrile (intermediate 73);

2-[3-chloro-4-[1-(4-chlorophenyl)-1-cyanoethyl]-5-methylphenyl]-2,3,4,5-tetrahydro-3,5-dioxo-1,2,4-triazine-6-carbonitrile (intermediate 74);

2-[5-chloro-4-[1-(4-chlorophenyl)-1-cyanoethyl]-2-methylphenyl]-2,3,4,5-tetrahydro-3,5-dioxo-1,2,4-triazine-6-carbonitrile (intermediate 75);

2-[4-[1-cyano-1-(4-fluorophenyl)ethyl]-3-fluorophenyl]-2,3,4,5-tetrahydro-3,5-dioxo-1,2,4-triazine-6-carbonitrile (intermediate 76);

2-[3,5-dichloro-4-[cyano(4-fluorophenyl)methyl]-phenyl]-2,3,4,5-tetrahydro-3,5-dioxo-1,2,4-triazine-6-carbonitrile (intermediate 77);

2-[3-chloro-4-[cyano(4-fluorophenyl)methyl]-5-methylphenyl]-2,3,4,5-tetrahydro-3,5-dioxo-1,2,4-triazine-6-carbonitrile (intermediate 78);

2-[4-[cyano(4-fluorophenyl)methyl]-3,5-dimethylphenyl]-2,3,4,5-tetrahydro-3,5-dioxo-1,2,4-triazine-6-carbonitrile (intermediate 79); and 2-[4-[(4-chlorophenyl)cyanomethyl]-3,5-dimethylphenyl]-2,3,4,5-tetrahydro-3,5-dioxo-1,2,4-triazine-6-carbonitrile (intermediate 80).

Following the same procedure and using the appropriate starting materials there are also prepared:

2-[3-chloro-4-[(4-chlorophenyl)cyanomethyl]phenyl]-2,3,4,5-tetrahydro-3,5-dioxo-1,2,4-triazine-6-carbonitrile (intermediate 81);

2-[3,5-dichloro-4-[(4-chlorophenyl)cyanomethyl]-phenyl]-2,3,4,5-tetrahydro-3,5-dioxo-1,2,4-triazine-6-carbonitrile (intemerdiate 82);

2-[3-chloro-4-[(4-chlorophenyl)cyanomethyl]-5-methylphenyl]-2,3,4,5-tetrahydro-3,5-dioxo-1,2,4-triazine-6-carbonitrile (intermediate 83);

2-[3-chloro-4-[(4-fluorophenyl)cyanomethyl]phenyl]-2,3,4,5-tetrahydro-3,5-dioxo-1,2,4-triazine-6-carbonitrile (intermediate 84); and 2-[3-chloro-4-[(4-methylphenyl)cyanomethyl]phenyl]-2,3,4,5-tetrahydro-3,5-dioxo-1,2,4-triazine-6-carbonitrile (intermediate 85).

EXAMPLE 9

A mixture of 6.86 parts of 2-[4-(1-cyano-1-phenylethyl)phenyl]-2,3,4,5-tetrahydro-3,5-dioxo-1,2,4-triazine-6-carbonitrile, 30 parts of concentrate hydrochloric acid and 150 parts of acetic acid was stirred and refluxed for 24 hours. The reaction mixture was evaporated and the residue was dissolved in trichloromethane. The latter was dried, filtered and evaporated, yielding 7.2 parts of 2-[4-(1-cyano-1-phenylethyl)phenyl]-2,3,4,5-tetrahydro-3,5-dioxo-1,2,4-triazine-6-carboxylic acid (intermediate 86).

In a similar manner there was also prepared:

2-[3-chloro-4-[1-(4-chlorophenyl)-1-cyanoethyl]-phenyl]-2,3,4,5-tetrahydro-3,5-dioxo-1,2,4-triazine-6-carboxylic acid (intermediate 87);

2-[3-chloro-4-[1-cyano-1-(4-fluorophenyl)ethyl]-phenyl]-2,3,4,5-tetrahydro-3,5-dioxo-1,2,4-triazine-6-carboxylic acid (intermediate 88);

2-[4-[1-(4-chlorophenyl)-1-cyanoethyl]-3-(trifluoromethyl)phenyl]-2,3,4,5-tetrahydro-3,5-dioxo-1,2,4-triazine-6-carboxylic acid (intemediate 89);

2-[4-[bis(4-chlorophenyl)cyanomethyl]-3-chloro-phenyl]-2,3,4,5-tetrahydro-3,5-dioxo-1,2,4-triazine-6-carboxylic acid (intermediate 90);

2-[3-chloro-4-[1-(4-chlorophenyl)-1-cyanobutyl]-phenyl]-2,3,4,5-tetrahydro-3,5-dioxo-1,2,4-triazine-6-carboxylic acid (intermediate 91);

2-[3-chloro-4-[1-(4-chlorophenyl)-1-cyanopentyl]-phenyl]-2,3,4,5-tetrahydro-3,5-dioxo-1,2,4-triazine-6-carboxylic acid (intermediate 92);

2-[3-chloro-4-[1-[4-chloro-3-(trifluoromethyl)phenyl]-1-cyanoethyl]phenyl]-2,3,4,5-tetrahydro-3,5-dioxo-1,2,4-triazine-6-carboxylic acid (intermediate 93);

2-[4-[1-(4-chlorophenyl)-1-cyanoethyl]-3,5-dichloro-phenyl]-2,3,4,5-tetrahydro-3,5-dioxo-1,2,4-triazine-6-carboxylic acid (intermediate 94);

2-[3-chloro-4-[1-(4-chlorophenyl)-1-cyanoethyl]-5-methylphenyl]-2,3,4,5-tetrahydro-3,5-dioxo-1,2,4-triazine-6-carboxylic acid (intermediate 95);

2-[5-chloro-4-[1-(4-chlorophenyl)-1-cyanoethyl]-2-methylphenyl]-2,3,4,5-tetrahydro-3,5-dioxo-1,2,4-triazine-6-carboxylic acid (intermediate 96);

2-[4-[1-cyano-1-(4-fluorophenyl)ethyl]-3-fluorophenyl]-2,3,4,5-tetrahydro-3,5-dioxo-1,2,4-triazine-6-carboxylic acid (intermediate 97);

2-[3,5-dichloro-4-[cyano(4-fluorophenyl)methyl]-phenyl]-2,3,4,5-tetrahydro-3,5-dioxo-1,2,4-triazine-6-carboxylic acid (intermediate 98);

2-[3-chloro-4-[cyano(4-fluorophenyl)methyl]-5-methylphenyl]-2,3,4,5-tetrahydro-3,5-dioxo-1,2,4-triazine-6-carboxylic acid (intermediate 99);

2-[4-[cyano(4-fluorophenyl)methyl]-3,5-dimethylphenyl]-2,3,4,5-tetrahydro-3,5-dioxo-1,2,4-triazine-6-carboxylic acid (intermediate 100); and 2-[4-[(4-chlorophenyl)cyanomethyl]-3,5-dimethylphenyl]-2,3,4,5-tetrahydro-3,5-dioxo-1,2,4-triazine-6-carboxylic acid (intermediate 101).

Following the same procedure and using the appropriate starting materials there are also prepared:

2-[3-chloro-4-[(4-chlorophenyl)cyanomethyl]phenyl]-2,3,4,5-tetrahydro-3,5-dioxo-1,2,4-triazine-6-carboxylic acid (intermediate 102);

2-[3,5-dichloro-4-[(4-chlorophenyl)cyanomethyl]phenyl]-2,3,4,5-tetrahydro-3,5-dioxo-1,2,4-triazine-6-carboxylic acid (intermediate 103);

2-[3-chloro-4-[(4-chlorophenyl)cyanomethyl]-5-methylphenyl]-2,3,4,5-tetrahydro-3,5-dioxo-1,2,4-triazine-6-carboxylic acid (intermediate 104);

2-[3-chloro-4-[(4-fluorophenyl)cyanomethyl]phenyl]-2,3,4,5-tetrahydro-3,5-dioxo-1,2,4-triazine-6-carboxylic acid (intermediate 105); and 2-[3-chloro-4-[(4-methylphenyl)cyanomethyl]phenyl]-2,3,4,5-tetrahydro-3,5-dioxo-1,2,4-triazine-6-carboxylic acid (intermediate 106).

EXAMPLE 10

To a stirred mixture of 16 parts of 2-[3-chloro-4-[(4-chlorophenyl)hydroxymethyl]phenyl]-1,2,4-triazine-3,5(2$\underline{H}$,4$\underline{H}$)-dione and 150 parts of trichloromethane were added dropwise, during a period of 5 minutes, 16 parts of thionyl chloride. Upon completion, stirring was continued for 3 hours at reflux temperature. The reaction mixture was evaporated in vacuo. Methylbenzene was added and the whole was evaporated again, yielding 14 parts (83.1%) of 2-[3-chloro-4-[chloro(4-chlorophenyl)methyl]phenyl]-1,2,4-triazine-3,5(2$\underline{H}$,4$\underline{H}$)-dione as a residue (intermediate 107).

In a similar manner there were also prepared:

2-[4-[chloro(4-chlorophenyl)methyl]-3,5-dichlorophenyl]-1,2,4-triazine-3,5-(2$\underline{H}$,4$\underline{H}$)-dione (intermediate 108);

2-[3-chloro-4-[chloro(4-chlorophenyl)methyl]-5-methylphenyl]-1,2,4-triazine-3,5-(2$\underline{H}$,4$\underline{H}$)-dione (intermediate 109);

2-[3-chloro-4-[chloro(4-fluorophenyl)methyl]phenyl]-1,2,4-triazine-3,5-(2$\underline{H}$,4$\underline{H}$)-dione (intermediate 110); and 2-[3-chloro-4-[chloro(4-methylphenyl)methyl]phenyl]-1,2,4-triazine-3,5-(2$\underline{H}$,4$\underline{H}$)-dione (intermediate 111).

Following the same procedure and using the appropriate starting materials there are also prepared:

2-[3-chloro-4-[1-chloro-1-(4-chlorophenyl)ethyl]-5-methylphenyl]-1,2,4-triazine-3,5-(2$\underline{H}$,4$\underline{H}$)-dione; (intermediate 112)

2-[4-(1-chloro-1-phenylethyl)phenyl]-1,2,4-triazine-3,5-(2$\underline{H}$,4$\underline{H}$)-dione (intermediate 113);

2-[3-chloro-4-[1-chloro-1-(4-chlorophenyl)ethyl]phenyl]-1,2,4-triazine-3,5-(2$\underline{H}$,4$\underline{H}$)-dione (intermediate 114);

2-[3-chloro-4-[1-chloro-1-(4-fluorophenyl)ethyl]phenyl]-1,2,4-triazine-3,5-(2$\underline{H}$,4$\underline{H}$)-dione (intermediate 115);

2-[4-[1-chloro-1-(4-chlorophenyl)ethyl]-3-(trifluoromethyl)phenyl]-1,2,4-triazine-3,5-(2$\underline{H}$,4$\underline{H}$)-dione (intermediate 116);

2-[4-[bis(4-fluorophenyl)chloromethyl]-3-(trifluoromethyl)phenyl]-1,2,4-triazine-3,5-(2$\underline{H}$,4$\underline{H}$)-dione (intermediate 117);

2-[3-chloro-4-[1-chloro-1-(4-chlorophenyl)butyl]phenyl]-1,2,4-triazine-3,5-(2$\underline{H}$,4$\underline{H}$)-dione (intermediate 118);

2-[3-chloro-4-[1-chloro-1-(4-chlorophenyl)pentyl]phenyl]-1,2,4-triazine-3,5-(2$\underline{H}$,4$\underline{H}$)-dione (intermediate 119);

2-[3-chloro-4-[1-chloro-1-[4-chloro-3-(trifluoromethyl)phenyl]ethyl]phenyl]-1,2,4-triazine-3,5-(2$\underline{H}$,4$\underline{H}$)-dione (intermediate 120);

2-[3,5-dichloro-4-[1-chloro-1-(4-chlorophenyl)ethyl]phenyl]-1,2,4-triazine-3,5-(2$\underline{H}$,4$\underline{H}$)-dione (intermediate 121);

2-[5-chloro-4-[1-chloro-1-(4-chlorophenyl)ethyl]-2-methylphenyl]-1,2,4-triazine-3,5-(2$\underline{H}$,4$\underline{H}$)-dione (intermediate 122);

2-[4-[1-chloro-1-(4-fluorophenyl)ethyl]-3-fluorophenyl]-1,2,4-triazine-3,5-(2$\underline{H}$,4$\underline{H}$)-dione (intermediate 123);

2-[3,5-dichloro-4-[chloro(4-fluorophenyl)methyl]phenyl]-1,2,4-triazine-3,5-(2$\underline{H}$,4$\underline{H}$)-dione (intermediate 124);

2-[3-chloro-4-[chloro(4-fluorophenyl)methyl]-5-methylphenyl]-1,2,4-triazine-3,5-(2$\underline{H}$,4$\underline{H}$)-dione (intermediate 125);

2-[4-[chloro(4-fluorophenyl)methyl]-3,5-dimethylphenyl]-1,2,4-triazine-3,5-(2$\underline{H}$,4$\underline{H}$)-dione (intermediate 126);

2-[4-[chloro(4-chlorophenyl)methyl]-3,5-dimethylphenyl]-1,2,4-triazine-3,5-(2$\underline{H}$,4$\underline{H}$)-dione (intermediate 127);

(B) Preparation of Final compounds

EXAMPLE 11

A mixture of 11.1 parts of 2-[3-chloro-4-[1-(4-chlorophenyl)-1-cyanoethyl]-5-methylphenyl]-2,3,4,5-tetrahydro-3,5-dioxo-1,2,4-triazine-6-carboxylic acid and 15 parts of 2-mercaptoacetic acid was stirred and heated for 2 hours at 180° C. The reaction mixture was cooled, water was added and the whole was treated with sodium hydrogen carbonate. The product was extracted with trichloromethane. The organic layer was dried, filtered and evaporated. The residue was purified by column chromatography over silica gel using a mixture of trichloromethane and methanol (95:5 by volume) as eluent. The pure fractions were collected and the eluent was evaporated in vacuo. The residue was stirred in 2,2′-oxybispropane. The product was filtered off and dried, yielding 5 parts (50%) of 2-chloro-α-(4-chlorophenyl)-4-(4,5-dihydro-3,5-dioxo-1,2,4-triazin-2(3$\underline{H}$)-yl)-α,6-dimethylbenzeneacetonitrile; mp. 226.7° C. (compound 1).

In a similar manner there were also prepared:
4-(4,5-dihydro-3,5-dioxo-1,2,4-triazin-2(3$\underline{H}$)-yl)-α-methyl-α-phenylbenzeneacetonitrile; mp. 189.2° C. (compound 2);

2-chloro-α-(4-chlorophenyl)-4-(4,5-dihydro-3,5-dioxo-1,2,4-triazin-2(3$\underline{H}$)-yl)-α-methylbenzeneacetonitrile; mp. 235.1° C. (compound 3);

2-chloro-4-(4,5-dihydro-3,5-dioxo-1,2,4-triazin-2(3$\underline{H}$)-yl)-α-(4-fluorophenyl)-α-methylbenzeneacetonitrile; mp. 202.8° C. (compound 4);

α-(4-chlorophenyl)-4-(4,5-dihydro-3,5-dioxo-1,2,4-triazin-2(3$\underline{H}$)-yl)-α-methyl-2-(trifluoromethyl)benzeneacetonitrile; mp. 232.8° C.; (compound 5);

α,α-bis(4-chlorophenyl)-2-chloro-4-(4,5-dihydro-3,5-dioxo-1,2,4-triazin-2(3$\underline{H}$)-yl)benzeneacetonitrile; mp. 229.9° C. (compound 6);

2-chloro-α-(4-chlorophenyl)-4-(4,5-dihydro-3,5-dioxo-1,2,4-triazin-2(3$\underline{H}$)-yl)-α-propylbenzeneacetonitrile; mp. 124.2° C.; (compound 7)

α-butyl-2-chloro-α-(4-chlorophenyl)-4-(4,5-dihydro-3,5-dioxo-1,2,4-triazin-2(3$\underline{H}$)-yl)-benzeneacetonitrile; mp. 126.3° C.; (compound 8)

4-chloro-α-[2-chloro-4-(4,5-dihydro-3,5-dioxo-1,2,4-triazin-2(3H)-yl)phenyl]-α-methyl-3-(trifluoromethyl)benzeneacetonitrile; mp. 233.7° C.; (compound 9)

2,6-dichloro-α-(4-chlorophenyl)-4-(4,5-dihydro-3,5-dioxo-1,2,4-triazin-2(3H)-yl)-α-methylbenzeneacetonitrile; mp. 184.5° C. (compound 10); and 2-chloro-α-(4-chlorophenyl)-4-(4,5-dihydro-3,5-dioxo-1,2,4-triazin-2-(3H)-yl)-α,5-dimethylbenzeneacetonitrile; mp. 285.8° C. (compound 11).

In a similar manner there were also prepared:

4-(4,5-dihydro-3,5-dioxo-1,2,4-triazin-2(3H)-yl)-2-fluoro-α-(4-fluorophenyl)-α-methylbenzeneacetonitrile; mp. 211.6° C. (compound 12);

2,6-dichloro-4-(4,5-dihydro-3,5-dioxo-1,2,4-triazin-2(3H)-yl)-α-(4-fluorophenyl)benzeneacetonitrile; mp. 250.2° C. (compound 13);

2-chloro-4-(4,5-dihydro-3,5-dioxo-1,2,4-triazin-2(3H)-yl)-α-(4-fluorophenyl)-6-methylbenzeneacetonitrile; mp. 222.8° C. (compound 14);

4-(4,5-dihydro-3,5-dioxo-1,2,4-triazin-2(3H)-yl)-α-(4-fluorophenyl)-2,6-dimethylbenzeneacetonitrile; mp. 272.3° C. (compound 15); and α-(4-chlorophenyl)-4-(4,5-dihydro-3,5-dioxo-1,2,4-triazin-2(3H)-yl)-2,6-dimethylbenzeneacetonitrile; mp. 259.6° C. (compound 16).

Following the same procedures and using the appropriate starting materials, there are also prepared:

2-chloro-α-(4-chlorophenyl)-4-(4,5-dihydro-3,5-dioxo-1,2,4-triazin-2(3H)-yl)benzeneacetonitrile; (compound 17)

2,6-dichloro-α-(4-chlorophenyl)-4-(4,5-dihydro-3,5-dioxo-1,2,4-triazin-2(3H)-yl)benzeneacetonitrile; (compound 18)

2-chloro-α-(4-chlorophenyl)-4-(4,5-dihydro-3,5-dioxo-1,2,4-triazin-2(3H)-yl)-6-methylbenzeneacetonitrile; (compound 19)

2-chloro-4-(4,5-dihydro-3,5-dioxo-1,2,4-triazin-2(3H)-α-(4-fluorophenyl)benzeneacetonitrile; (compound 20) and 2-chloro-4-(4,5-dihydro-3,5-dioxo-1,2,4-triazin-2(3H)-yl)-α-(4-methylphenyl)benzeneacetonitrile; (compound 21).

EXAMPLE 12

A mixture of 12 parts of 2-[3-chloro-4-[chloro(4-chlorophenyl)methyl]phenyl]-1,2,4-triazine-3,5(2H,4H)-dione and 5.4 parts of copper cyanide was stirred and heated first for 3 hours at 130° C. and for 3 hours at 180° C. After cooling, the precipitated product was dissolved in a mixture of trichloromethane and methanol (90:10 by volume). The inorganic precipitate was filtered off and the filtrate was evaporated in vacuo. The residue was purified four times by column chromatography over silica gel using first a mixture of trichloromethane and acetonitrile (90:10 by volume), second a mixture of tetrachloromethane and methanol (93:7 by volume) and then twice a mixture of tetrachloromethane and acetonitrile (95:5 by volume) as eluent. The pure fractions were collected and the eluent was evaporated. The residue was further purified by column chromatography (HPLC) over silica gel using a mixture of trichloromethane and methanol (98:2 by volume) as eluent. The pure fractions were collected and the eluent was evaporated in vacuo. The residue was dried, yielding 1.3 parts (11.2%) of 2-chloro-α-(4-chlorophenyl)-4-(4,5-dihydro-3,5-dioxo-1,2,4-triazin-2(3H)-yl)benzeneacetonitrile; mp. 196.8° C. (compound 22).

In a similar manner there were also prepared:

2,6-dichloro-α-(4-chlorophenyl)-4-(4,5-dihydro-3,5-dioxo-1,2,4-triazin-2(3H)-yl)benzeneacetonitrile; mp. 290.5° C. (compound 23);

2-chloro-α-(4-chlorophenyl)-4-(4,5-dihydro-3,5-dioxo-1,2,4-triazin-2(3H)-yl)-6-methylbenzeneacetonitrile; mp. 267.2° C. (compound 24);

2-chloro-4-(4,5-dihydro-3,5-dioxo-1,2,4-triazin-2(3H)-yl)-α-(4-fluorophenyl)benzeneacetonitrile; mp. 185.2° C. (compound 25); and 2-chloro-4-(4,5-dihydro-3,5-dioxo-1,2,4-triazin-2(3H)-yl)-α-(4-methylphenyl)benzeneacetonitrile; mp. 162.3° C. (compound 26).

Following the same procedures and using equivalent amounts of the appropriate starting materials there are also prepared:

2-chloro-α-(4-chlorophenyl)-4-(4,5-dihydro-3,5-dioxo-1,2,4-triazin-2(3H)-yl)-α,6-dimethylbenzeneacetonitrile (compound 27).

4-(4,5-dihydro-3,5-dioxo-1,2,4-triazin-2(3H)-yl)-α-methyl-α-phenylbenzeneacetonitrile; (compound 28);

2-chloro-α-(4-chlorophenyl)-4-(4,5-dihydro-3,5-dioxo-1,2,4-triazin-2(3H)yl)-α-methylbenzeneacetonitrile (compound 29);

2-chloro-4-(4,5-dihydro-3,5-dioxo-1,2,4-triazin-2(3H)-yl)-α-(4-fluorophenyl)-α-methylbenzeneacetonitrile (compound 30);

α-(4-chlorophenyl)-4-(4,5-dihydro-3,5-dioxo-1,2,4-triazin-2(3H)-yl)-α-methyl-2-(trifluoromethyl)benzeneacetonitrile (compound 31);

α,α-bis(4-chlorophenyl)-2-chloro-4-(4,5-dihydro-3,5-dioxo-1,2,4-triazin-2(3H)-yl)benzeneacetonitrile (compound 32);

2-chloro-α-(4-chlorophenyl)-4-(4,5-dihydro-3,5-dioxo-1,2,4-triazin-2(3H)-yl)-α-propylbenzeneacetonitrile (compound 33);

α-butyl-2-chloro-α-(4-chlorophenyl)-4-(4,5-dihydro-3,5-dioxo-1,2,4-triazin-2(3H)-yl)benzeneacetonitrile; (compound 34);

4-chloro-α-[2-chloro-4-(4,5-dihydro-3,5-dioxo-1,2,4-triazin-2(3H)-yl)phenyl]-α-methyl-3-(trifluoromethyl)benzeneacetonitrile (compound 35);

2,6-dichloro-α-(4-chlorophenyl)-4-(4,5-dihydro-3,5-dioxo-1,2,4-triazin-2(3H)-yl)-α-methylbenzeneacetonitrile; (compound 36);

2-chloro-α-(4-chlorophenyl)-4-(4,5-dihydro-3,5-dioxo-1,2,4-triazin-2(3H)-yl)-α,5-dimethylbenzeneacetonitrile; (compound 37);

4-(4,5-dihydro-3,5-dioxo-1,2,4-triazin-2(3H)-yl)-2-fluoro-α-(4-fluorophenyl)-α-methylbenzeneacetonitrile (compound 38);

2,6-dichloro-4-(4,5-dihydro-3,5-dioxo-1,2,4-triazin-2(3H-yl)-α-(4-fluorophenyl)benzeneacetonitrile (compound 39);

2-chloro-4-(4,5-dihydro-3,5-dioxo-1,2,4-triazin-2(3H)-yl)-α-(4-fluorophenyl)-6-methylbenzeneacetonitrile (compound 40);

4-(4,5-dihydro-3,5-dioxo-1,2,4-triazin-2(3H)-yl)-α-(4-fluorophenyl)-2,6-dimethylbenzeneacetonitrile (compound 41); and α-(4-chlorophenyl)-4-(4,5-dihydro-3,5-dioxo-1,2,4-triazin-2(3H)-yl)-2,6-dimethylbenzeneacetonitrile (compound 42).

(C) Pharmacological Examples

The strong anti-protozoal activity of the compounds of formula (I), the pharmaceutically acceptable acid addition salts and the possible stereochemically isomeric forms thereof is clearly evidenced by the data obtained in the following experiments, which data are only given to illustrate the useful anti-protozoal properties of all the compounds embraced within the invention and not to limit the invention either with respect to the scope of the susceptible Protozoa nor with respect to the scope of formula (I).

EXAMPLE 13

Outline of anticoccidial efficacy test against *Eimeria tenella*

Hisex chickens were fed with a commercial basal ration not containing a coccidiostatic agent.

Eighteen-day-old chickens were sorted in groups of two birds. Water was supplied automatically and medicated feed was supplied ad libitum from the day of infection (day 0) until the seventh day (not included) after infection. Unmedicated feed was supplied ad libitum to two groups of four birds for uninfected and infected controls.

Unmedicated feed was a commercial basal ration not containing a coccidiostatic agent. Medicated feed was prepared from unmedicated feed by thoroughly mixing the latter with an amount of the tested compound.

On day 0 the birds were inoculated orally with $10^5$ sporulated oocysts of *Eimeria tenella*. On day 5 the faecal score was determined and graded:
0 = no blood spots
1 = one or two blood spots
2 = three to five blood spots
3 = more than five blood spots On the seventh day oocyst production is determined by collecting the feces and the oocyst count per gram feces (OPG) and the birds are weighed.

In table 1 the first column shows the average relative weight gain in percent compared with the non-infected controls. The second column shows the average faecal score and the third column illustrates the average oocyst count.

TABLE 1

| Comp. No. | dose of tested compound in ppm in feed | average relative weight gain | average faecal score | average oocyst count (OPG) × 1000 |
|---|---|---|---|---|
| 1 | 100 | 92 | 0 | 0 |
|   | 10 | 99 | 0 | 0 |
|   | 5 | 96 | 0 | 0 |
| 2 | 100 | 93 | 0 | 0 |
| 3 | 100 | 94 | 0 | 0 |
|   | 10 | 92 | 0 | 0 |
| 4 | 100 | 103 | 0 | 0 |
|   | 10 | 100 | 0 | 0 |
|   | 5 | 92 | 1.0 | 0 |
| 5 | 100 | 94 | 0 | 0 |
|   | 10 | 92 | 0.8 | 0 |
| 6 | 100 | 98 | 0 | 0 |
|   | 10 | 97 | 1.5 | 0 |
| 10 | 10 | 97 | 0 | 0 |
|   | 5 | 98 | 0 | 0 |
|   | 1 | 94 | 0.5 | 0 |
| * | — | 100 | 0 | 0 |
| ** | — | 78 | 2.9 | 459 |
| 13 | 1 | 101 | 0 | 0 |
|   | 0.5 | 96 | 0 | 0 |
| 14 | 1 | 98 | 0 | 0 |
| 15 | 100 | 99 | 0 | 0 |
|   | 10 | 99 | 0 | 0 |

TABLE 1-continued

| Comp. No. | dose of tested compound in ppm in feed | average relative weight gain | average faecal score | average oocyst count (OPG) × 1000 |
|---|---|---|---|---|
| 16 | 100 | 94 | 0 | 0 |
|   | 10 | 97 | 0 | 0 |
|   | 5 | 94 | 0 | 0 |
| 22 | 100 | 98 | 0 | 0 |
|   | 10 | 102 | 0 | 0 |
|   | 5 | 100 | 0 | 0 |
|   | 1 | 98 | 1.0 | 0 |
|   | 0.5 | 97 | 0.5 | 0 |
| 23 | 100 | 98 | 0 | 0 |
|   | 10 | 101 | 0 | 0 |
|   | 5 | 98 | 0 | 0 |
|   | 1 | 102 | 0 | 0 |
|   | 0.5 | 97 | 0.1 | 0 |
| 24 | 100 | 99 | 0 | 0 |
|   | 10 | 108 | 0 | 0 |
|   | 5 | 99 | 0 | 0 |
|   | 1 | 99 | 0 | 0 |
|   | 0.5 | 94 | 0.4 | 0 |
| 25 | 100 | 95 | 0 | 0 |
|   | 10 | 99 | 0 | 0 |
|   | 5 | 100 | 0 | 0 |
|   | 1 | 94 | 0.2 | 0 |
| 26 | 100 | 92 | 0 | 0 |
|   | 10 | 95 | 0.5 | 0 |

* = non-infected control
** = infected control

EXAMPLE 14

Outline of anticoccidial efficacy test against *Eimeria acervulina*

Hisex chickens were fed with a commercial basal ration not containing a coccidiostatic agent.

Eighteen-day-old chickens were sorted in groups of four birds. Water was supplied automatically and medicated feed was supplied ad libitum from the day of infection (day 0) until the seventh day (not included) after infection. Unmedicated feed was supplied ad libitum to two groups of four birds for uninfected and infected controls.

Unmedicated feed was a commercial basal ration not containing a coccidiostatic agent. Medicated feed was prepared from unmedicated feed by thoroughly mixing the latter with an amount of the tested compound.

On day 0 the birds were inoculated orally with $2.10^6$ sporulated oocysts of *Eimeria acervulina*. On day 4 and 5 the faecal score was determined and graded:
0 = normal
1 = slightly soft faeces
2 = white watery diarrhea
3 = slimy mucoid diarrhea On the fifth and sixth day oocyst production is determined by collecting the feces and the oocyst count per gram feces (OPG) and the birds are weighed.

In table 2 the first column shows the average relative weight gain in percent compared with the non-infected controls. The second column shows the average faecal score and the third column illustrates the average oocyst count.

TABLE 2

| Comp. No. | dose of tested compound in ppm in feed | average relative weight gain | average faecal score | average oocyst count (OPG) × 1000 |
|---|---|---|---|---|
| 1 | 100 | 81 | 0.4 | 0 |
| * | — | 100 | 0 | 0 |
| ** | — | 73 | 2.8 | 356 |
| 3 | 100 | 98 | 0 | 0 |
|   | 10 | 84 | 1.1 | 147 |

TABLE 2-continued

| Comp. No. | dose of tested compound in ppm in feed | average relative weight gain | average faecal score | average oocyst count (OPG) × 1000 |
|---|---|---|---|---|
| 4 | 100 | 97 | 0 | 0 |
|  | 10 | 86 | 1.1 | 35 |
|  | 5 | 92 | 1.0 | 0 |
| 5 | 100 | 94 | 0 | 0 |
| 6 | 100 | 91 | 0 | 3 |
| 10 | 100 | 85 | 0.2 | 0 |
|  | 10 | 85 | 0.3 | 14 |
|  | 5 | 90 | 1.2 | 33 |
| 12 | 100 | 97 | 0.3 | 0 |
| 13 | 100 | 97 | 0 | 0 |
|  | 10 | 97 | 0.3 | 28 |
|  | 5 | 94 | 0.3 | 14 |
|  | 1 | 93 | 0.3 | 55 |
| 14 | 100 | 99 | 0 | 0 |
|  | 10 | 102 | 0 | 5 |
| 15 | 100 | 99 | 0 | 0 |
|  | 10 | 95 | 0.5 | 44 |
| 16 | 100 | 94 | 0 | 0 |
|  | 10 | 91 | 0.1 | 20 |
| 22 | 100 | 94 | 0 | 0 |
|  | 10 | 91 | 0.2 | 11 |
|  | 5 | 101 | 0 | 23 |
| 23 | 100 | 99 | 0 | 0 |
|  | 10 | 99 | 0 | 0 |
|  | 5 | 102 | 0 | 6 |
|  | 1 | 100 | 0 | 29 |
|  | 0.5 | 90 | 0.7 | 17 |
| 24 | 100 | 98 | 0 | 0 |
|  | 10 | 92 | 0 | 10 |
|  | 5 | 96 | 0 | 0 |
|  | 1 | 92 | 0.5 | 44 |
| 25 | 100 | 98 | 0 | 0 |
|  | 10 | 97 | 0.1 | 36 |

\* = non-infected control
\*\* = infected control

What we claim is:

1. A chemical compound of formula

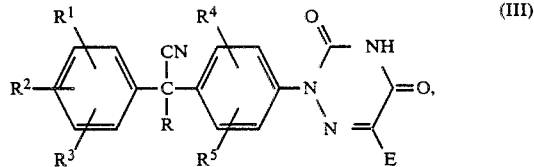

the acid addition salts and possible stereochemically isomeric forms thereof, wherein:

$R^1$, $R^2$ and $R^3$ are each independently hydrogen, halo, trifluoromethyl, $C_{1-6}$ alkyl, $C_{1-6}$ alkyloxy, $C_{1-6}$ alkylthio or $C_{1-6}$ alkylsulfonyl;

$R^4$ and $R^5$ are each independently hydrogen, halo, trifluoromethyl or $C_{1-6}$ alkyl; and R is hydrogen, $C_{1-6}$ alkyl, cyclo $C_{3-6}$ alkyl or phenyl optionally substituted with up to three substituents each independently selected from the group consisting of halo, trifluoromethyl, $C_{1-6}$ alkyl, $C_{1-6}$ alkyloxy, $C_{1-6}$ alkylthio and $C_{1-6}$ alkylsulfonyloxy;

E is an electron attracting group selected from the group consisting of carboxyl, sulfonyloxy, sulfinyloxy, amido, cyano, $C_{1-6}$ alkylsulfonyl, phenylsulfonyloxy, $C_{1-6}$ alkylphenylsulfonyloxy, halophenylsulfonyloxy and $C_{1-6}$ alkyloxycarbonyl.

2. A chemical compound according to claim 1, wherein E is carboxyl.

3. A chemical compound according to claim 1, wherein E is cyano, $C_{1-6}$ alkyloxycarbonyl or amido.

4. A chemical compound having the formula

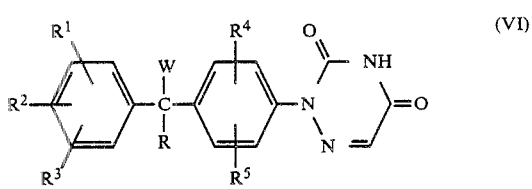

the acid addition salts and stereochemically isomeric forms thereof, wherein:

$R^1$, $R^2$ and $R^3$ are each independently hydrogen, halo, trifluromethyl, $C_{1-6}$ alkyl, $C_{1-6}$ alkyloxy, $C_{1-6}$ alkylthio or $C_{1-6}$ alkylsulfonyl;

$R^4$ and $R^5$ are each independently hydrogen, halo, trifluromethyl or $C_{1-6}$ alkyl;

R is hydrogen, $C_{1-6}$ alkyl, cyclo $C_{3-6}$ alkyl or phenyl optionally substituted with up to three substituents each independently selected from the group consisting of halo, trifluoromethyl, $C_{1-6}$ alkyl, $C_{1-6}$ alkyloxy, $C_{1-6}$ alkylthio and $C_{1-6}$ alkylsulfonyloxy; and W is a member selected from the group consisting of halo, methylsulfonyloxy and 4-methylphenylsulfonyloxy.

5. A chemical compound according to claim 4, wherein $R^1$ and $R^2$ are each independently hydrogen, halo, trifluoromethyl, or $C_{1-6}$ alkyl; $R^3$ is hydrogen; R is hydrogen, $C_{1-6}$ alkyl, phenyl, or halophenyl; and $R^4$ and $R^5$ are each independently hydrogen, halo, trifluromethyl or $C_{1-6}$ alkyl.

6. A chemical compound according to claim 5, wherein $R^1$ is halo; $R^2$ and $R^3$ are both hydrogen; and R is hydrogen, $C_{1-6}$ alkyl or halophenyl.

7. A chemical compound according to claim 6, wherein $R^1$ is 4-halo; R is hydrogen or methyl; and $R^4$ and $R^5$ are each independently hydrogen, halo, methyl or trifluoromethyl, said $R^4$ and $R^5$ being substituted on the 2 and 6 position of the phenyl moiety bearing said $R^4$ and $R^5$.

* * * * *